United States Patent [19]
Rogers

[11] Patent Number: 6,030,800
[45] Date of Patent: Feb. 29, 2000

[54] URINE CANCER TEST

[76] Inventor: Sam S. Rogers, 1643 N. Ashland Ave., Chicago, Ill. 60622

[21] Appl. No.: 09/329,164

[22] Filed: Jun. 9, 1999

[51] Int. Cl.[7] ............................... C12Q 1/62; C12Q 1/00
[52] U.S. Cl. ................................... 435/10; 435/4
[58] Field of Search ............................. 435/10, 4

[56] References Cited

PUBLICATIONS

Wang et al; "Chung–hua I Hsueh Chien Yen Tsa Chih"; vol. 3(2), p. 93 (Abstract) 1980.

*Primary Examiner*—Louise N. Leary
*Attorney, Agent, or Firm*—Cook, Alex, McFarron, Manzo Cummings & Mehler, Ltd.

[57] ABSTRACT

A urine test for cancer is disclosed for the detection of a broad spectrum of cancers in which the specimen of urine from the subject to be tested is placed into a test tube, a concentrated acid is added to the specimen and the resulting mixture is heated to the boiling point. The mixture is then cooled to ambient temperature, ethyl ether is added and mixed well into the mixture and the mixture is left to stand. The change in color of the mixture of from pink to purple indicates the presence of cancer in the subject and no change in color indicates the absence of cancer.

11 Claims, No Drawings

URINE CANCER TEST

BACKGROUND AND SUMMARY OF THE INVENTION

The present invention is directed to a test for the detection of a broad spectrum of cancers and, more specifically, to a method of testing for the presence or absence of cancer in mammals by analyzing a urine specimen from the subject mammal.

Although some test procedures have been conducted on urine to determine the presence of bladder cancer, no test is known to the inventor in which a urine specimen may be analyzed to detect a broad spectrum of diverse forms of cancer in the mammalian subject from which the urine specimen was obtained.

It would be highly advantageous if a simple diagnostic test was available in which a urine specimen provided by the subject to be tested could be simply, inexpensively and non-invasively tested to determine whether the individual might have any one of a broad spectrum of different cancers, or whether the subject was cancer free of any such cancers at the time of the test. The purpose of the present invention is to realize these advantages.

In the present invention, a urine specimen from the mammalian subject to be tested may be simply, inexpensively, non-invasively and quickly and reliably tested to determine whether or not the individual does or does not have any one of a wide and diverse spectrum of cancers at the time of testing.

In one principal aspect of the present invention, a method for detecting the presence of cancer in a mammal comprises depositing a specimen of urine from the subject mammal to be tested into a container and adding a concentrated acid to the specimen of urine in the container. The specimen of urine with the acid therein is heated to its boiling point and then allowed to cool to ambient temperature. After cooling, ethyl ether is added to the ambient temperature specimen of urine with the acid therein, and mixed thoroughly therewith. The resulting mixed liquid is permitted to stand and then the presence or absence of cancer in the subject mammal is determined by observing the color of the liquid after standing.

In another principal aspect of the present invention, the concentrated acid is hydrochloric acid.

In still another principal aspect of the present invention, the volume ratio of the acid to the specimen of urine is about 0.1:1 to 0.6:1.

In still another principal aspect of the present invention, the volume ratio of the ethyl ether to the specimen of urine is about 0.04:1 to 0.2:1.

In still another principal aspect of the present invention, the mixing of the liquid following the addition of the ethyl ether is by shaking.

In still another principal aspect of the present invention, the purity of the acid and the ethyl ether is at least USP grade.

In another principal aspect of the present invention, the presence of cancer is exhibited by the mixed liquid in the container changing color to a color of pink to purple, and the absence of cancer is exhibited by the color of the mixed liquid in the container remaining unchanged.

These and other objects, features and advantages of the present invention will be more clearly understood through a consideration of the following detailed description.

DESCRIPTION OF THE PREFERRED EMBODIMENT

In the preferred method of the present invention, a specimen of urine from the subject to be tested is placed in a container. The container may, for example, be a test tube of about ½ inch in diameter and about 5 inches in length, and the specimen may fill about ½ to ¾ of the test tube.

A concentrated acid, preferably of at least USP grade, is added to the specimen of urine in the container. The acid is preferably hydrochloric acid and is added in the amount of about 1.5–4.5 cc to the specimen of urine in the container which is at room temperature. The volume ratio of concentrated acid to the specimen of urine is preferably between about 0.1:1 to 0.6:1.

The specimen of urine with the acid therein is then heated from ambient room temperature to its boiling point by suitable heating means, for example a Bunsen burner. Once the boiling point is reached, the heating is ceased and the heated urine and acid mixture is then allowed to again cool to ambient room temperature.

Upon reaching ambient room temperature, ethyl ether, also preferably of at least USP grade, is added to the urine and acid mixture and is mixed thoroughly therewith, for example, by shaking.

This mixed liquid is then allowed to stand for a sufficient period of time for a color change to develop, if a change is to develop. If no change in color develops within the first 10–15 minutes of standing, the mixed liquid is permitted to stand for preferably up to about one hour total to insure that no color change will develop.

In the present invention it has been discovered, that if the mixed liquid comprising the heated and then cooled mixture of urine and acid, together with the subsequently added ethyl ether, changes in color to pink to purple, the subject mammal from which the specimen has been obtained has cancer somewhere within its body. This cancer may be any one of a wide range of spectrum of diverse cancers including, for example lung, liver, uterine and pancreatic cancers and leukemia. The color change may be confined to a narrow band of from ⅛–¼ inches in the center of the specimen, the remainder of which is substantially clear in color, or it may consist of an overall color change of the entire specimen of urine which may be cloudy, but of a pink to purple color. In either event, the subject from which the specimen was taken will have cancer somewhere within its body. Conversely, if no color change is observed at the conclusion of the test, the subject is cancer free.

EXAMPLE

Urine specimens were obtained from 50 persons at a hospital. Unknown to the individual conducting the test according to the present invention, 20 of the persons who provided specimens to be analyzed had previously been diagnosed with any one of several forms of cancer, including colon, lung, liver and uterine cancers and leukemia. The remaining 30 specimens were from persons who had either never previously been diagnosed for cancer and/or may have had observed conditions which may or may not be cancerous, e.g. colon polyps, lung spots, etc.

The specimens of urine obtained from each of these 50 persons were individually analyzed according to the invention. Each specimen was added to a test tube approximately 5 inches long and ½ inch in diameter in an amount sufficient to fill the test tube approximately ¾ full. To this specimen was added 1.5 cc of concentrated hydrochloric acid, and the urine and acid mixture was then heated over a Bunsen burner to bring it up to the boiling point of the mixture. This heated mixture was then cooled to ambient room temperature, at which point 0.5 cc of ethyl ether was added and the mixture was shaken well.

Within 10–15 minutes, 40 of the 50 specimens tested had changed colors to anywhere from various tones of pink to, in one instance, a very dark pink/purple. The remaining 10 specimens remained unchanged in color after standing for at least one hour.

Up to this point, the analyses of the specimens which had been conducted by the person performing the analyses had been blind tests, i.e. the person had not been given any information with respect to the gender, age or condition of the 50 subjects from whom the specimens were obtained. At the conclusion of the 50 tests, the results were compared to the individual subject's medical history at which time the following observations were made.

Of the 40 specimens in which a color change to pink was observed, 20 of the subjects who provided the specimens had previously been diagnosed with any one of several different forms of cancer, including colon, lung, liver or uterine cancer or leukemia. In fact, the single specimen which turned dark pink/purple was from a leukemia patient who was terminal at the time of the test, and who passed away soon after the analyses were performed.

Of the remaining 20 test specimens that showed a color change, the subjects who provided the specimens had not previously been specifically diagnosed with cancer. However, several of these subjects had been observed to have conditions which may or may not be cancerous, e.g. colon polyps, lung spots, etc. It is significant that in a follow-up of these 20 patients one year after the analyses were performed, each of the 20 had subsequently been diagnosed with cancer, including colon, lung, liver and pancreatic cancer. At least some of these determinations were subsequently made by biopsy of the conditions which had previously been observed, e.g. the colon polyps or lung spots.

Also of significance, the subjects who provided the 10 remaining specimens that showed no color change during the tests neither had previously been diagnosed with cancer, had exhibited any evidence of any condition that might be cancerous, e.g. colon polyps or lung spots, and after the one year follow-up, were not reported to have developed cancer or any condition that might be determined upon further testing to be cancerous.

It will be understood that the preferred embodiment of the present invention which has been described is merely illustrative of the principles of the present invention. Modifications may be made by those skilled in the art without departing from the true spirit and scope of the invention.

I claim:

1. A method for detecting the presence of cancer in a mammal comprising:
   depositing a specimen of urine from the subject mammal to be tested into a container;
   adding a concentrated acid to the specimen of urine in the container;
   heating the specimen of urine with the acid therein to its boiling point;
   cooling the heated specimen of urine with the acid therein to ambient temperature;
   adding ethyl ether to the ambient temperature specimen of urine with the acid therein, and mixing the resulting liquid thoroughly; and
   allowing the mixed liquid to stand and then determining the presence or absence of cancer in the subject mammal by observing the color of the liquid after standing.

2. The method of claim 1, wherein the concentrated acid is hydrochloric acid.

3. The method of claim 1, wherein the volume ratio of the concentrated acid to the specimen of urine is about 0.1:1 to 0.6:1.

4. The method of claim 3, wherein the volume ratio of the ethyl ether to the specimen of urine is about 0.04:1 to 0.2:1.

5. The method of claim 1, wherein the volume ratio of the ethyl ether to the specimen of urine is about 0.04:1 to 0.2:1.

6. The method of claim 1, wherein the mixing of the resulting liquid is by shaking.

7. The method of claim 1, wherein the purity of the concentrated acid and the ethyl ether is at least of USP grade.

8. The method of claim 1, wherein the concentrated acid is hydrochloric acid, the volume ratio of the acid to the specimen of urine is about 0.1:1 to 0.6:1; the volume ratio of the ethyl ether to the specimen of urine is about 0.04:1 to 0.2:1, and wherein the purity of the acid and the ethyl ether is at least of USP grade.

9. The method of claim 8, wherein the mixing of the resulting liquid is by shaking.

10. The method of claim 8, wherein the presence of cancer is exhibited by the mixed liquid in the container changing color to a color of pink to purple, and the absence of cancer is exhibited by the color of the mixed liquid in the container remaining unchanged.

11. The method of claim 1, wherein the presence of cancer is exhibited by the mixed liquid in the container changing color to a color of pink to purple, and the absence of cancer is exhibited by the color of the mixed liquid in the container remaining unchanged.

* * * * *